US007658998B2

(12) United States Patent
Brown et al.

(10) Patent No.: US 7,658,998 B2
(45) Date of Patent: Feb. 9, 2010

(54) METHOD OF PREPARING SUSTAINED RELEASE MICROPARTICLES

(75) Inventors: Josiah Brown, Somerville, MA (US); Warren E. Jaworowicz, Bolton, MA (US); Gregory C. Troiano, Weymouth, MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 993 days.

(21) Appl. No.: 10/762,220

(22) Filed: Jan. 21, 2004

(65) Prior Publication Data

US 2004/0247870 A1 Dec. 9, 2004

Related U.S. Application Data

(60) Provisional application No. 60/441,946, filed on Jan. 22, 2003.

(51) Int. Cl.
*B32B 5/66* (2006.01)
(52) U.S. Cl. .................... 428/403; 428/407; 427/213.3; 427/213.31; 427/213.32; 427/213.33; 427/213.34; 427/213.35; 514/12; 514/13; 514/14; 514/15; 514/16; 530/303; 530/304; 424/489
(58) Field of Classification Search ............ 427/213.32, 427/213.3, 213.31, 213.33, 213.34, 213.35; 514/12–16; 530/303, 304; 428/403; 424/489
See application file for complete search history.

(56) References Cited

U.S. PATENT DOCUMENTS

| | | | |
|---|---|---|---|
| 4,293,539 A | 10/1981 | Ludwig et al. | |
| 4,734,416 A | 3/1988 | Banno et al. | |
| 4,804,663 A | 2/1989 | Kennis et al. | |
| 5,006,528 A | 4/1991 | Oshiro et al. | |
| 5,019,400 A | 5/1991 | Gombotz et al. | |
| 5,192,741 A * | 3/1993 | Orsolini et al. ............... 514/4 |
| 5,229,382 A | 7/1993 | Chakrabarti et al. | |
| 5,439,688 A | 8/1995 | Orsolini et al. | |
| 5,792,477 A | 8/1998 | Rickey et al. | |
| 5,817,343 A | 10/1998 | Burke | |
| 5,922,253 A | 7/1999 | Herbert et al. | |
| 6,183,781 B1 | 2/2001 | Burke | |
| 6,342,250 B1 | 1/2002 | Masters | |
| 6,379,704 B2 | 4/2002 | Wright et al. | |
| 6,455,074 B1 | 9/2002 | Tracy et al. | |
| 6,495,164 B1 | 12/2002 | Ramstack et al. | |
| 2002/0076437 A1 | 6/2002 | Kothari et al. | |

FOREIGN PATENT DOCUMENTS

| | | | |
|---|---|---|---|
| WO | WO 89/05138 | | 6/1989 |
| WO | 92/19226 | * | 11/1992 |
| WO | WO 92/19226 | | 11/1992 |
| WO | 94/07469 | * | 4/1994 |
| WO | WO 94/07469 | | 4/1994 |

OTHER PUBLICATIONS

Tabata et al "Injectable Polyanhydride Granules . . . " Journal of Pharmaceutical Sciences 83: 5-11, Jan. 1994.*
Anderson, L., et al., "An Injectable Sustained Release Fertility Control System," *Contraception*, 13(3): 375-385 (Mar. 1976).
Gangadharam, P. R. J., et al., "Sustained Release of Isoniazid In Vivo from a Single Implant of a Biodegradable Polymer," *Tubercle*, 72:115-122 (Jun. 1991).
Gresser, J. D., et al., "Larger Animal Testing of an Injectable Sustained Release Fertility Control System," *Contraception*, 17(3):253-266 (Mar. 1978).
Tabata, Y., et al., "A Formulation Method Using D,L-Lactic Acid Oligomer for Protein Release with Reduced Initial Burst," *Journal of Controlled Release*, 23:55-63 (1993).
Tabata, Y., et al., "Injectable Polyanhydride Granules Provide Controlled Release of Water-Soluble Drugs with a Reduced Initial Burst," *Journal of Pharmaceutical Sciences*, 83:5-11 (Jan. 1994).
Wang, H. T., et al., "Degradation of Poly(ester) Microspheres," *Biomaterials*,11:679-685 (Nov. 1990).
Wise, D. L., "Development of Drug Delivery Systems for Use in Treatment of Narcotic Addition—A Culmination," *Biopolymeric Controlled Release Systems*, CRC Press, Inc. (Boca Raton, FL) Chapter 8:115-181 (1984).
Yolles, S., et al., "Controlled Release of Biologically Active Agents," *Controlled Release Polymeric Formulations—ACS Symposium Series 33*, 171st Meeting of the American Chemical Society, New York, NY, Apr. 7-9, 1976.
Sharon, A. C. and Wise, D. L., "Development of Drug Delivery Systems for Use in Treatment of Narcotic Addiction," *NIDA Research Monograph*, 28:194-213 (1981).

* cited by examiner

*Primary Examiner*—Leszek Kilman
(74) *Attorney, Agent, or Firm*—Hamilton, Brook, Smith & Reynolds, P.C.

(57) ABSTRACT

The present invention relates to a method for preparing an injectable composition of microparticles for the sustained release of a biologically active agent. The microparticles include a biocompatible polymer and a biologically active agent. The invention provides an improved process for the preparation of microparticles, wherein the physical characteristics of the microparticles, for example, the morphology, density and size, are independent of the process used to prepare the initially formed polymer/drug matrix. The method includes the steps of (a) providing a polymer/biologically active agent matrix; (b) compressing the polymer/biologically active agent matrix, thereby forming a compressed matrix; and (c) fragmenting the compressed matrix, thereby forming an injectable microparticle composition. The polymer/drug matrix can be provided by any suitable method.

42 Claims, 6 Drawing Sheets

METHOD OF PREPARING SUSTAINED RELEASE MICROPARTICLES

RELATED APPLICATION

This application claims the benefit of U.S. Provisional Patent Application No. 60/441,946, filed Jan. 22, 2003, the entire contents of which are incorporated herein by reference.

GOVERNMENT SUPPORT

The invention was supported, in whole or in part, by a grant (Grant No. 1 R43 DA13531-01A1) from the National Institute on Drug Abuse (NIDA) at the National Institutes of Health (NIH). The Government has certain rights in the invention.

BACKGROUND OF THE INVENTION

Many illnesses or conditions require administration of a constant or sustained level of a medicament or biologically active agent to provide the desired prophylactic or therapeutic effect. This may be accomplished through a multiple dosing regimen or by employing a system that releases the medicament in a sustained fashion.

Attempts to sustain medication levels include the use of biodegradable materials, such as polymeric matrices, containing the medicament. The use of these matrices, for example, in the form of microparticles or microcarriers, can provide sustained release of medicaments by utilizing the inherent biodegradability of the polymer. The ability to provide a sustained level of medicament can result in improved patient compliance. For example, patient compliance can be particularly difficult in the treatment of affective disorders such as schizophrenia, depression, anxiety and in view of the large outpatient population and altered psychological state of the patient.

Certain methods of fabricating polymer-based sustained release devices comprise the steps of dissolving a polymer in a solvent, adding to the polymer solution the active agent to be incorporated and removing the solvent from the mixture, thereby forming a matrix of the polymer with the active agent distributed throughout the matrix. However, the physical characteristics of the microparticles, for example, the morphology, density and size, are significantly dependent upon all steps used in the method of preparation making control and tailoring of the physical characteristics of the resulting microparticles a difficult (sometimes impossible) and expensive undertaking.

For example, many sustained release compositions can exhibit an increased release of biologically active agent over the first twenty-four hours after administration, commonly referred to as a burst. In some instances, this burst can result in an undesirable increase in the levels of biologically active agent and/or minimal release of agent thereafter. Tailoring of the physical characteristics of the microparticles to provide an improved release can require modification of the entire process of preparation. Therefore, a need exists for methods of preparing sustained release microparticles where additional control over release kinetics by, for example, reducing the burst of agent and/or providing an improved release profile can be exerted.

SUMMARY OF THE INVENTION

The present invention relates to a method for preparing an injectable composition of microparticles for the sustained release of a biologically active agent. The microparticles include a biocompatible polymer and a biologically active agent, for example, a therapeutic, prophylactic or diagnostic agent, also referred to herein as a "drug." The invention provides an improved process for the preparation of microparticles wherein the physical characteristics of the microparticles, for example, the morphology, density and size, are independent of the process used to prepare the initially formed polymer/drug matrix. That is, the method of the invention provides for the ability to decouple the fabrication of the polymer/drug matrix from subsequent steps used to impart the desired physical characteristics to the injectable microparticles.

The method includes the steps of: (a) providing a polymer/biologically active agent matrix; (b) compressing the polymer/biologically active agent matrix, thereby forming a compressed matrix; and (c) fragmenting the compressed matrix, thereby forming an injectable microparticle composition. The polymer/biologically active agent matrix can be provided by any suitable method.

In one embodiment, the polymer/biologically active agent matrix is provided by (a) preparing a mixture of a biologically active agent, a biocompatible polymer and a solvent, e.g., a polymer solvent; and (b) removing the solvent, thereby forming the polymer/biologically active agent matrix. The biologically active agent can be suspended (e.g., completely or partially suspended) in the mixture and/or dissolved (e.g., completely or partially dissolved) in the mixture.

As such, in one embodiment the invention relates to a method for preparing an injectable microparticle composition for the sustained release of a biologically active agent comprising the steps of: (a) preparing a mixture comprising a biologically active agent, a biocompatible polymer, and a solvent, thereby forming a single phase solvent system; (b) removing the solvent from the solution, thereby forming a polymer/biologically active agent matrix; (c) compressing the matrix using confined pressure compaction, thereby forming a compressed matrix; and (d) fragmenting the matrix, thereby forming the injectable microparticle composition.

In a preferred embodiment, compression of the polymer/biologically active agent matrix is conducted without the application of heat. For example, the compression is conducted at or below the transition temperature of the matrix. In one embodiment, the matrix is compressed at about ambient temperature (e.g., room temperature such as about 15° C. to about 30° C.). In another embodiment, the matrix is compressed at or below room temperature. In one embodiment, fragmenting of the compressed matrix is conducted at or below the transition temperature of the polymer/biologically active agent matrix.

In a preferred embodiment, the biologically active agent is an antipsychotic drug such as aripiprazole, olanzapine or risperidone.

In one embodiment, the polymer/biologically active agent matrix is provided by (a) preparing a mixture of a biologically active agent, a biocompatible polymer, and a solvent, e.g., a polymer solvent; (b) forming droplets of the mixture; (c) solidifying the droplets (e.g., freezing), thereby forming solid droplets (e.g., frozen droplets); and (d) extracting the solvent present in the solid droplets into a non-solvent, thereby forming the polymer/biologically active agent matrix.

The present invention also relates to sustained release microparticles that are formed by the methods described herein. The microparticles include a biocompatible polymer such as, for example, poly(lactic acid) or a poly(lactic acid-co-glycolic acid) copolymer, and a biologically active agent, for example, a therapeutic, prophylactic or diagnostic agent such as a protein, peptide, nucleic acid or small organic molecule (e.g., an antipsychotic agent).

In a particularly preferred embodiment, the microparticles prepared according the method of the invention include a biocompatible polymer and a drug used to treat affective disorders, such as schizophrenia, depression, and anxiety. Suitable drugs for treating affective disorders include, but are not limited to, risperidone, olanzapine and aripiprazole.

In one embodiment, the microparticles can further include one or more excipients and/or release modifiers. The particles can include one or more additional drugs.

Practice of the present invention can be used to prepare microparticles by using any suitable method of preparing the polymer/biologically active agent matrix followed by downstream tailoring of the physical characteristics of the resulting injectable microparticles. For example, the morphology and/or size of the initially fabricated polymer/biologically active agent matrix is decoupled from the physical characteristics of the resulting microparticles, which can impact the injectability and release profile of the microparticles.

For example, the present invention allows the production of dense microparticles for drug delivery. In one embodiment, the porosity of the polymer/drug matrix is reduced and thus a given volume of microparticles formed in accordance with the processes described herein contains a higher drug load than an equivalent volume of polymer/biologically active agent matrix. Thus, practice of the present invention can be used to increase drug loads for a given dose volume.

Therefore, the improved method described herein provides for an efficient, facile and cost effective preparation of sustained release microparticles having desirable physical properties. For example, the microparticles prepared according to the methods described herein can exhibit a reduced initial release of biologically active agent, a higher sustained level of agent and/or a longer duration of release of the biologically active agent following administration.

DETAILED DESCRIPTION OF THE INVENTION

Figure 1:
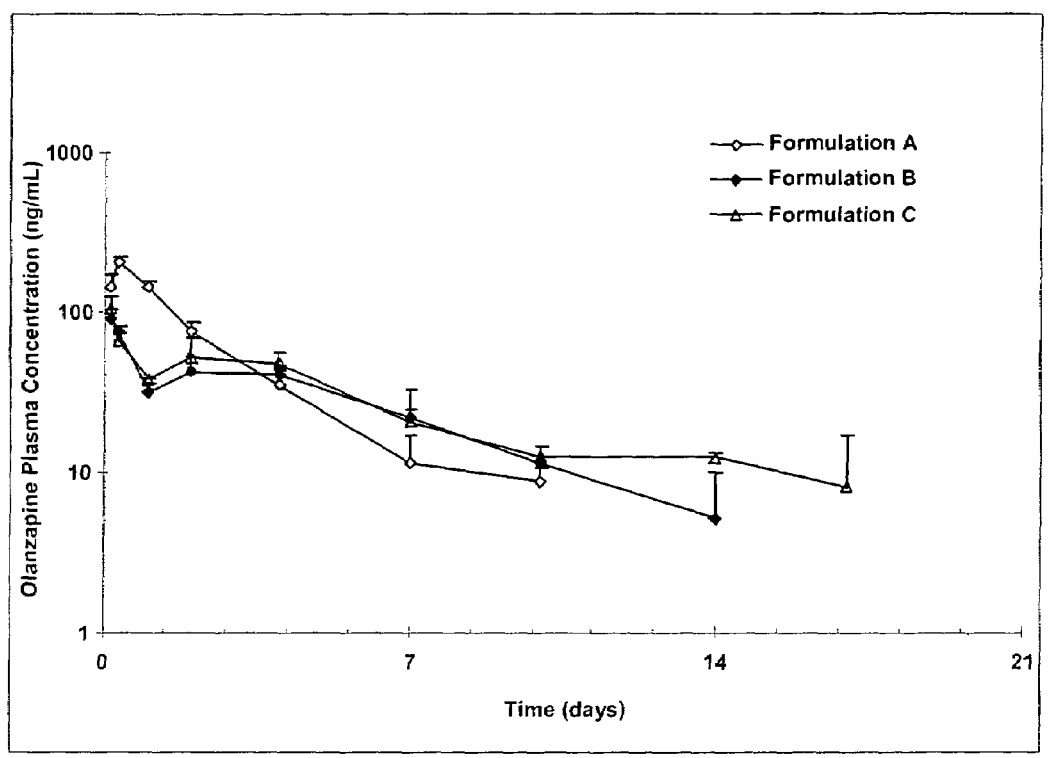
FIG. 1 is a plot of olanzapine concentration in blood plasma (nanograms/milliliter) versus time (days) for an in vivo study of three polymer/drug microparticle compositions (50 milligrams olanzapine/kilogram normalized dose) administered subcutaneously to Sprague-Dawley rats.

The foregoing and other objects, features and advantages of the invention will be apparent from the following more particular description of preferred embodiments of the invention.

The present invention relates to a method for preparing an injectable composition of microparticles for the sustained release of a biologically active agent. The microparticles include a biocompatible polymer and a biologically active agent, for example, a therapeutic, prophylactic or diagnostic agent, also referred to herein as a "drug." The invention provides an improved process for the preparation of microparticles wherein the physical characteristics of the microparticles, for example, the morphology, density and size, are independent of the process used to prepare the initially formed polymer/biologically active agent matrix. That is, the method of the invention provides for the ability to decouple the fabrication of the polymer/biologically active agent matrix from subsequent steps used to impart the desired physical characteristics to the injectable microparticles.

The method includes the steps of: (a) providing a polymer/biologically active agent matrix; (b) compressing the polymer/biologically active agent matrix, thereby forming a compressed matrix; and (c) fragmenting the compressed matrix, thereby forming an injectable microparticle composition. The polymer/biologically active agent matrix can be provided by any suitable method. A suitable method should not result in a significant reduction of the biological activity of the incorporated drug. As such, in embodiments wherein the drug is a labile agent, for example, a biologically active agent that can undergo degradation when exposed to heat or solvent, the polymer/biologically active agent matrix can be prepared at a temperature which does not significantly reduce the biological activity of the drug. The method can further include the step of fragmenting the polymer/biologically active agent matrix prior to compressing the matrix, referred to herein as "precompression fragmenting."

In one embodiment, the polymer/biologically active agent matrix is provided by (a) preparing a mixture of a biologically active agent, a biocompatible polymer and a solvent, e.g., a polymer solvent; and (b) removing the solvent, thereby forming the polymer/biologically active agent matrix. The biologically active agent can be suspended (e.g., completely or partially suspended) in the mixture and/or dissolved (e.g., completely or partially dissolved) in the mixture. For example, the solvent can be a solvent for both the biologically active agent and the biocompatible polymer, e.g., both the biologically active agent and the polymer are dissolved in the solvent. In one embodiment, the mixture constitutes a single phase solvent system.

As such, in one embodiment the invention relates to a method for preparing an injectable microparticle composition for the sustained release of a biologically active agent comprising the steps of: (a) preparing a mixture comprising a biologically active agent, a biocompatible polymer, and a solvent, thereby forming a single phase solvent system; (b) removing the solvent from the solution, thereby forming a polymer/biologically active agent matrix; (c) compressing the matrix using confined pressure compaction, thereby forming a compressed matrix; and (d) fragmenting the matrix, thereby forming the injectable microparticle composition.

The term "single phase solvent system," as used herein, refers to a mixture that includes one or more liquids, e.g., solvents, that are in a single phase and in which the polymer and biologically active agent are dissolved and/or suspended. When a combination of liquids is used, the liquids of the combination are miscible and when the liquids are mixed, a single phase, rather than separate phases, results. For example, when a combination of solvents is used, the solvents of the combination are miscible. A combination of liquids, e.g., solvents, can be formed prior to, following, or simultaneously with the mixing of the polymer and/or agent with the solvent or solvents to form a single phase solvent system. In a preferred embodiment, the solvent used is a single solvent.

In a preferred embodiment, compressing the polymer/biologically active agent matrix is conducted without the application of heat. For example, the compression can be conducted at or below the transition temperature of the matrix. In one embodiment, the matrix is compressed at about ambient temperature or room temperature (e.g., such as about 15° C. to about 30° C.). In one embodiment, fragmenting of the compressed matrix is conducted at or below the transition temperature of the polymer/biologically active agent matrix.

In a preferred embodiment, the biologically active agent is an antipsychotic drug such as aripiprazole, olanzapine or risperidone.

In one embodiment, the polymer/biologically active agent matrix is provided by (a) preparing a mixture of a biologically active agent, a biocompatible polymer, and a solvent, e.g., a polymer solvent; (b) forming droplets of the mixture; (c) solidifying the droplets (e.g., freezing), thereby forming solid droplets (e.g., frozen droplets); and (d) extracting the solvent present in the solid droplets into a non-solvent, thereby forming the polymer/biologically active agent matrix. The matrix can then be filtered and dried.

The present invention also relates to the sustained release microparticles that are formed by the methods described herein. The microparticles include a biocompatible polymer such as, for example, poly(lactic acid) or a poly(lactic acid-co-glycolic acid) copolymer, and a biologically active agent, for example, a therapeutic, prophylactic or diagnostic agent such as a protein, peptide, nucleic acid or small organic molecule.

In a particularly preferred embodiment, the microparticles prepared according the method of the invention include a biocompatible polymer and a drug used to treat affective disorders, such as schizophrenia, depression, and anxiety. Suitable drugs for treating affective disorders include, but are not limited to, risperidone, olanzapine and aripiprazole.

In one embodiment, the microparticles can further include one or more excipients and/or release modifiers. The particles can include one or more additional drugs.

The invention also relates to use of the microparticles prepared according to the described method for the manufacture of a medicament for use in therapy. For example, for use in treating affective disorders such as schizophrenia, depression and anxiety.

Preparation of Polymer/Drug Matrix

The terms "polymer/biologically active agent matrix" and "polymer/drug matrix," as used interchangeably herein, refer to a solid material comprising a biocompatible polymer (e.g., a homopolymer, copolymer or polymer blend) and drug molecules, which are dispersed throughout the polymer. The polymer/biologically active agent matrix can be of any size and shape prior to compression and fragmenting. For example, the polymer/biologically active agent matrix can be a film, pellet, cylinder, disc or particle (e.g., spherical, non-spherical or irregularly shaped). The polymer/drug matrix can be homogeneous or heterogeneous, for example, the polymer/drug matrix can have a homogeneous distribution of drug in the matrix or, alternatively, the distribution of drug in the matrix can be heterogeneous. The polymer/drug matrix can further comprise excipients such as, for example, surfactants, carbohydrates (e.g., monosaccharides and polysaccharides), release modifying agents, stabilizers, one or more additional biologically active agents and any combination thereof.

Any suitable method can be used to provide the polymer/drug matrix for subsequent fragmentation and compression to form an injectable microparticle composition.

In one embodiment, the polymer/biologically active agent matrix is provided by (a) forming a mixture of a biologically active agent, a biocompatible polymer and a solvent, e.g., a polymer solvent, and (b) removing the solvent, thereby forming a polymer/biologically active agent matrix. The biologically active agent can be in solution and/or suspended in the mixture. In one embodiment, the drug and polymer are dissolved and/or suspended in a single phase solvent system. A number of methods are known for providing the polymer/drug matrix in this manner.

For example, methods for forming a composition for the sustained release of biologically active agent are described in U.S. Pat. No. 5,019,400, issued to Gombotz, et al., on May 28, 1991; U.S. Pat. No. 5,922,253 issued to Herbert, et al., on Jul. 13, 1999; and U.S. Pat. No. 6,455,074 issued to Tracy, et al., on Sep. 24, 2002, the entire contents of each of which are incorporated herein by reference.

In this method, a mixture comprising a biologically active agent, a biocompatible polymer and a polymer solvent is processed to create droplets, wherein at least a significant portion of the droplets contains polymer, polymer solvent and the active agent. These droplets are then frozen by a suitable means. Examples of means for processing the mixture to form droplets include directing the dispersion through an ultrasonic nozzle, pressure nozzle, Rayleigh jet, or by other known means for creating droplets from a solution.

Means suitable for freezing droplets include directing the droplets into or near a liquified gas such as liquid argon or liquid nitrogen to form frozen microdroplets which are then separated from the liquified gas. The frozen microdroplets are then exposed to a liquid or solid non-solvent such as ethanol, hexane, ethanol mixed with hexane, heptane, ethanol mixed with heptane, pentane or oil.

The solvent in the frozen microdroplets is extracted as a solid and/or liquid into the non-solvent to form a polymer/active agent matrix comprising a biocompatible polymer and a biologically active agent. Mixing ethanol with other non-solvents, such as hexane, heptane or pentane, can increase the rate of solvent extraction, above that achieved by ethanol alone, from certain polymers such as, for example, poly(lactide-co-glycolide) polymers.

A wide range of sizes of polymer/drug matrices can be made by varying the droplet size, for example, by changing the ultrasonic nozzle diameter. If the polymer/drug matrix is in the form of particles and very large particles are desired, the particles can be extruded, for example, through a syringe directly into the cold liquid. Increasing the viscosity of the polymer solution can also increase the polymer/drug matrix (e.g., particle) size. The size of the polymer/drug matrices (e.g., particles) which can be produced by this process ranges, for example, from about 1 micrometer to greater than about 1000 micrometers in diameter.

Yet another method of forming a polymer/drug matrix from a suspension or solution comprising a biocompatible polymer and a biologically active agent includes film casting, such as in a mold, to form a film or a shape. For instance, after putting the suspension into a mold, the polymer solvent is then removed (e.g., via evaporation or sublimation) or the temperature of the polymer suspension is reduced (e.g., the polymer suspension is frozen) until a film or shape is obtained. Means for removing the solvent from a cast film are known in the art and include vacuum drying, lyophilization, flash drying, and sublimation, among others. The solvent is removed until the residual solvent levels are brought to concentrations that are suitable for administration to a patient. One of ordinary skill in the art can determine the concentrations of residual solvent in particles administered to a patient that are acceptable or tolerated without undue experimentation.

A further example of a process for the production of a polymer/drug matrix, e.g., particles, is disclosed in U.S. Pat. No. 3,737,337, incorporated by reference herein in its entirety, wherein a solution of a wall or shell forming polymeric material in a solvent is prepared. The solvent is only partially miscible in water. A solid or core material is dissolved or dispersed in the polymer-containing mixture and, thereafter, the core material-containing mixture is dispersed in an aqueous liquid that is immiscible in the organic solvent in order to remove solvent from the polymer/drug matrix, e.g., particles.

Another example of a process in which solvent is removed from particles containing a substance is disclosed in U.S. Pat. No. 3,523,906, incorporated herein by reference in its entirety. In this process, a material to be encapsulated is emulsified in a solution of a polymeric material in a solvent that is immiscible in water and then the emulsion is emulsified in an aqueous solution containing a hydrophilic colloid. Solvent removal from the particles is then accomplished by evaporation and the product is obtained.

In still another process, as shown in U.S. Pat. No. 3,691,090, incorporated herein by reference in its entirety, organic solvent is evaporated from a dispersion of particles in an aqueous medium, preferably under reduced pressure.

Similarly, the disclosure of U.S. Pat. No. 3,891,570, incorporated herein by reference in its entirety, shows a method in which solvent from a dispersion of particles in a polyhydric alcohol medium is evaporated from the particles by the application of heat or by subjecting the particles to reduced pressure.

Another example of a solvent removal process is shown in U.S. Pat. No. 3,960,757, incorporated herein by reference in its entirety.

Tice et al., in U.S. Pat. No. 4,389,330, incorporated herein by reference in its entirety, describe the preparation of particles containing an active agent by a method including: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming particles containing the active agent in the suspension; and (d) extracting the remainder of the solvent from the particles.

Solvent and/or solvent/nonsolvent systems suitable for production of a polymer/drug matrix can be determined via routine experimentation using techniques well known to those of ordinary skill in the art.

Suitable solvents for forming a poly(lactic acid-co-glycolic acid) polymer solution/drug mixture, for example, a dispersion of an agent in a polymer solution, or alternatively, a polymer/drug solution, e.g., an agent co-dissolved with polymer as a single phase solvent system, include methylene chloride, acetone, ethyl acetate, methyl acetate, tetrahydrofuran, dimethylsulfoxide (DMSO), acetonitrile, and chloroform.

In another embodiment, the polymer/drug matrix can be provided by mixing one or more dry polymers with one or more dry biologically active agents. In yet another embodiment, the polymer/drug matrix may be supplied by purchasing the material from a commercial supplier.

As used herein, the terms "a" and "an" refer to one or more.

As used herein, the term "particle size" refers to a number median diameter as determined by conventional particle size measuring techniques known to those skilled in the art such as, for example, laser diffraction, photon correlation spectroscopy, sedimentation field flow fractionation, disk centrifugation or electrical sensing zone method. Laser diffraction is preferred. The "number median diameter" reflects the distribution of particles (by number) as a function of particle diameter. An alternative designation of particle size often used in the art is the "volume median diameter." The volume median diameter is the median diameter of the volume weighted size distribution, also referred to as $D_{v,50}$. The volume median diameter reflects the distribution of volume as a function of particle diameter.

An "injectable microparticle," as defined herein, comprises a biocompatible polymer component having a volume median particle size from about 1 to about 1000 microns and having a biologically active agent dispersed therein. For example, the particle size can be about 500 microns or less, such as about 400, 300, 200 or about 100 microns or less. The microparticles can be of any shape, for example, spherical, non-spherical or irregular shape, and are suitable for administration by any means (e.g., by needle, needle-free delivery, or inhalation). It is understood that injectable refers to a size range of the microparticle rather than the mode of administration employed to deliver the microparticles to a patient.

The term "release modifying agent," as used herein, refers to a material which, when incorporated into a polymer/drug matrix, modifies the drug-release characteristics of the matrix. A release modifying agent can, for example, either decrease or increase the rate of drug release from the matrix. One group of release modifying agents includes metal-containing salts, as disclosed in U.S. Pat. No. 5,656,297 issued to Bernstein, et al., on Aug. 12, 1997, the contents of which are incorporated herein by reference.

"Sustained release," as that term is used herein, is release of biologically active agent from the injectable microparticles which occurs over a period which is longer than the period during which a biologically significant amount of agent would be available following direct administration of a solution of agent. In one embodiment, a sustained release is a release of agent which occurs over a period of at least about one day such as, for example, at least about 2, 4, 6, 8, 10, 15, 20, 30, 60, or at least about 90 days. A sustained release of agent can be a continuous or a discontinuous release, with relatively constant or varying rates of release. The continuity of release and level of release can be affected by the type of polymer composition used (e.g., monomer ratios, molecular weight, block composition, and varying combinations of polymers), protein loading, and/or selection of excipients to produce the desired effect.

"Sustained release" is also referred to in the art as "modified release," "prolonged release," "long acting release ('LAR')," or "extended release." "Sustained release," as used herein, also encompasses "sustained action" or "sustained effect." "Sustained action" and "sustained effect," as those terms are used herein, refer to an increase in the time period over which an agent performs its therapeutic, prophylactic or diagnostic activity as compared to an appropriate control. "Sustained action" is also known to those experienced in the art as "prolonged action" or "extended action."

The sustained release profile of the injectable microparticles prepared according to the method described herein can exhibit a reduced initial release of biologically active agent, a higher sustained level of agent and/or a longer duration of release of the agent following administration.

Without being bound by a particular theory, it is believed that the release of the biologically active agent can occur by two different mechanisms. First, the biologically active agent can be released by diffusion through aqueous liquid-filled channels generated in the polymer matrix, such as by the dissolution of the biologically active agent or by voids created by the removal of the polymer solvent during the preparation of the sustained release composition. A second mechanism is the release of the biologically active agent due to degradation of the polymer.

The rate of polymer and/or particle degradation can be controlled, in part, by changing polymer properties that influence the rate of hydration of the polymer. These properties include, for example, the ratio of lactide to glycolide; the isomeric form of the polymer, e.g., the use of the L-isomer of a monomer instead of a racemic mixture; and the molecular weight of the polymer. These properties can affect hydrophilicity and crystallinity, which control the rate of hydration of the polymer.

By altering the properties of the polymer, the contributions of diffusion and/or polymer/particle degradation to biologically active agent release can be controlled. For example, increasing the glycolide content of a poly(lactide-co-glycolide) polymer and decreasing the molecular weight of the polymer can enhance the hydrolysis of the polymer and thus can provide an increased biologically active agent release from polymer erosion. Without being held to any particular theory, it is believed that the morphology and/or density of the polymer matrix can also effect the diffusion of an agent from the microparticles and/or the degradation of the microparticle or its constituent polymer.

Polymers which can be used in the formulation of polymer/drug matrix microparticles include any polymer which is biocompatible. Biocompatible polymers suitable for use in the present invention include biodegradable and non-biodegradable polymers and blends and copolymers thereof, as described herein. A polymer is biocompatible if the polymer and any degradation products of the polymer are non-toxic to the recipient and also possess no significant deleterious or untoward effects on the recipient's body, such as a significant immunological reaction at the injection site.

"Biodegradable," as defined herein, means the composition will degrade or erode in vivo to form smaller chemical species. Degradation can result, for example, by enzymatic, chemical and physical processes. Suitable biocompatible, biodegradable polymers include, for example, poly(lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or poly-ethylene glycol and polyorthoester, biodegradable polyurethane, blends thereof, and copolymers thereof.

Suitable biocompatible, non-biodegradable polymers include non-biodegradable polymers such as, for example, polyacrylates, polymers of ethylene-vinyl acetates and other acyl substituted cellulose acetates, non-degradable polyurethanes, polystyrenes, polyvinylchloride, polyvinyl fluoride, poly(vinyl imidazole), chlorosulphonate polyolefins, polyethylene oxide, blends thereof, and copolymers thereof, such as PLG-co-EMPO described in copending U.S. patent application Ser. No. 09/886,394 entitled "Functionalized Degradable Polymer" and filed on Jun. 22, 2001, the entire contents of which is hereby incorporated by reference.

Further, the terminal functionalities or pendant groups of the polymers can be modified, for example, to modify hydrophobicity, hydrophilicity and/or to provide, remove or block moieties which can interact with the active agent via, for example, ionic or hydrogen bonding.

In a preferred embodiment of the present invention, the polymer used to produce the particles is a poly(lactic acid-co-glycolic acid) ("PLG") copolymer. The poly(lactic acid-co-glycolic acid) polymer includes d-, l-, or racemic forms of the polymer, for example, in some embodiments the polymer used is poly(d,l-lactic acid-co-glycolic acid). In some embodiments, the poly(lactic acid-co-glycolic acid) contains free carboxyl end groups. In other embodiments, the poly (lactic acid-co-glycolic acid) contains alkyl ester end groups such as methyl ester end groups.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weight is of about 2,000 Daltons to about 2,000,000 Daltons. In a preferred embodiment, the polymer is a biodegradable polymer or copolymer. In a more preferred embodiment, the polymer is a poly(lactide-co-glycolide) which can have a lactide: glycolide ratio of about 25:75 to about 85:15, e.g., about 25:75, about 50:50, about 75:25, or about 85:15, and a molecular weight of about 5,000 Daltons to about 150,000 Daltons. In an even more preferred embodiment, the molecular weight of the PLG used in the present invention has a molecular weight of about 5,000 Daltons to about 42,000 Daltons.

The term "biologically active agent," as used herein, is an agent or its pharmaceutically acceptable salt which, when released in vivo, possesses the desired biological activity, for example, therapeutic, diagnostic and/or prophylactic properties in vivo. It is understood that the term includes stabilized biologically active agents as described herein. The terms "biologically active agent," "therapeutic, prophylactic or diagnostic agent," "drug," "active agent," and "agent" are used interchangeably herein. Preferably, the drug is soluble in the solvent or combination of solvents that also dissolve the polymer.

Examples of suitable biologically active agents include, but are not limited to, antipsychotic agents such as aripiprazole, risperidone, and olanzapine; antitumor agents such as bleomycin hydrochloride, carboplatin, methotrexate and adriamycin; antibiotics such as gentamicin, tetracycline hydrochloride and ampicillin; antipyretic, analgesic and anti-inflammatory agents; antitussives and expectorants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenytoin and ethosuximide; antiulcer agents such as metoclopramide; antidepressants such as clomipramine; antiallergic agents such as diphenhydramine; cardiotonics such as theophillol; antiarrythmic agents such as propranolol hydrochloride; vasodilators such as diltiazem hydrochloride and bamethan sulfate; hypotensive diuretics such as pentolinium and ecarazine hydrochloride; antidiuretic agents such as metformin; anticoagulants such as sodium citrate and sodium heparin; hemostatic agents such as thrombin, menadione sodium bisulfite and acetomenaphthone; antituberculous agents such as isoniazide and ethanbutol; hormones such as prednisolone sodium phosphate and methimazole; and narcotic antagonists such as nalorphine hydrochloride.

Additional biologically active agents suitable for use in the invention include, but are not limited to, proteins, muteins and active fragments thereof, such as immunoglobulins, antibodies, cytokines (e.g., lymphokines, monokines, chemokines), interleukins, interferons ($\beta$-IFN, $\alpha$-IFN and $\gamma$-IFN), erythropoietin, nucleases, tumor necrosis factor, colony stimulating factors, insulin, enzymes (e.g., superoxide dismutase, tissue plasminogen activator), tumor suppressors, blood proteins, hormones and hormone analogs (e.g., growth hormone, adrenocorticotropic hormone and luteinizing hormone releasing hormone (LHRH)), vaccines (e.g., tumoral, bacterial and viral antigens), antigens, blood coagulation factors; growth factors; peptides such as protein inhibitors, protein antagonists, and protein agonists; nucleic acids, such as antisense molecules; oligonucleotides; and ribozymes.

In a particular embodiment, the biologically active agent is a labile drug. As used herein, "labile drug" refers to a drug which loses a substantial amount of activity when either warmed to elevated temperatures, such as temperatures greater than physiological temperatures (e.g., about 37° C.), or dissolved in an organic solvent or in solution at an aqueous/organic interface. Examples of labile drugs can include proteins, peptides and nucleic acids. By decoupling the process of forming the polymer/drug matrix from the final product morphology, the present processes enable formation of the polymer/drug matrix using variety of matrix formation techniques such as those that employ low temperatures, e.g., room temperature or below, while still producing injectable microparticles for sustained release of the labile agent. In addition, the instant processes enable the formation of the polymer/drug matrix using various solvent systems such as, for example, forming the matrix without mixing the drug with an organic solvent.

The microparticles prepared according to the invention can contain from about 0.01% (w/w) to about 90% (w/w) of the biologically active agent (dry weight of composition). The amount of agent can vary depending upon the desired effect of the agent, the planned release levels, and the time span over which the agent is to be released. A preferred range of agent loading is about 0.1% (w/w) to about 75% (w/w), for example, about 0.1% (w/w) to about 60% (w/w). A more preferred range of agent loading is about 0.5% (w/w) to about 75% (w/w) agent, for example, about 0.5% (w/w) to about 60% (w/w).

In one embodiment, the biologically active agent is stabilized. The biologically active agent can be stabilized against degradation, loss of potency and/or loss of biological activity, all of which can occur during formation of the sustained release composition having the biologically active agent dispersed therein, and/or prior to and during in vivo release of the biologically active agent. In one embodiment, stabilization can result in a decrease in the solubility of the biologically active agent, the consequence of which is a reduction in the initial release of biologically active agent, in particular, when release is from a sustained release composition. In addition, the period of release of the biologically active agent can be prolonged.

Stabilization of the biologically active agent can be accomplished, for example, by the use of a stabilizing agent or a specific combination of stabilizing agents. The stabilizing agent can be present in the mixture. "Stabilizing agent," as that term is used herein, is any agent which binds or interacts in a covalent or non-covalent manner or is included with the biologically active agent. Stabilizing agents suitable for use in the invention are described in U.S. Pat. Nos. 5,716,644 and 5,674,534 to Zale, et al.; U.S. Pat. Nos. 5,654,010 and 5,667,808 to Johnson, et al.; U.S. Pat. Nos. 5,711,968 to Tracy, et al., and 6,265,389 to Burke, et al.; and in copending U.S. patent application Ser. No. 08/934,830 by Burke, et al., filed on Sep. 22, 1997, the entire teachings of each of which are incorporated herein by reference.

For example, a metal cation can be complexed with the biologically active agent, or the biologically active agent can be complexed with a polycationic complexing agent such as protamine, albumin, spermidine and spermine, or associated with a "salting-out" salt. In addition, a specific combination of stabilizing agents and/or excipients may be needed to optimize stabilization of the biologically active agent. For example, when the biologically active agent in the mixture is an acid-stable or free sulfhydryl-containing protein such as $\beta$-IFN, a particular combination of stabilizing agents which includes a disaccharide and an acidic excipient can be added to the mixture. This type of stabilizing formulation is described in detail in U.S. Pat. No. 6,465,425 issued to Tracy, et al., on Oct. 15, 2002, the entire contents of which is incorporated herein by reference.

Suitable metal cations include any metal cation capable of complexing with the biologically active agent. A metal cation-stabilized biologically active agent, as defined herein, comprises a biologically active agent and at least one type of metal cation wherein the cation is not significantly oxidizing to the biologically active agent. In a particular embodiment, the metal cation is multivalent, for example, having a valency of +2 or more. If the agent is metal cation-stabilized, it is preferred that the metal cation is complexed to the biologically active agent.

Suitable stabilizing metal cations include biocompatible metal cations. A metal cation is biocompatible if the cation is non-toxic to the recipient in the quantities used and also presents no significant deleterious or untoward effects on the recipient's body such as a significant immunological reaction at the injection site. The suitability of metal cations for stabilizing biologically active agents and the ratio of metal cation to biologically active agent needed can be determined by one of ordinary skill in the art by performing a variety of stability indicating techniques such as polyacrylamide gel electrophoresis, isoelectric focusing, reverse phase chromatography, and High Performance Liquid Chromatography (HPLC) analysis on particles of metal cation-stabilized biologically active agents prior to and following particle size reduction and/or encapsulation. The molar ratio of metal cation to biologically active agent is typically between about 1:2 and about 100:1, preferably between about 2:1 and about 12:1.

Examples of stabilizing metal cations include, but are not limited to, $K^+$, $Zn^{+2}$, $Mg^{+2}$ and $Ca^{+2}$. Stabilizing metal cations also include cations of transition metals such as $Cu^{+2}$. Combinations of metal cations can also be employed. For example, in one embodiment, $Zn^{+2}$ is used as a stabilizing metal cation for bovine serum albumin (herein "BSA") at a zinc cation component to BSA molar ratio of about 4:1 to about 100:1. In a preferred embodiment, the zinc cation component to BSA molar ratio is about 4:1 to about 12:1, and most preferably 10:1.

The biologically active agent can also be stabilized with at least one polycationic complexing agent. Suitable polycationic complexing agents include, but are not limited to, protamine, spermine, spermidine and albumin. The suitability of polycationic complexing agents for stabilizing biologically active agents can be determined by one of ordinary skill in the art in the manner described above for stabilization with a metal cation. An equal weight ratio of polycationic complexing agent to biologically active agent is suitable.

Further, excipients can be added to the compositions of the present invention such as, for example, to maintain the potency of the biologically active agent over the duration of release and to modify polymer degradation. One or more excipients can be added to the mixture which is then used to form the polymer/biologically active agent matrix. For example, an excipient may be suspended or dissolved along with polymer and agent in a solvent system prior to formation of the polymer drug matrix. Alternatively, excipient(s) can be mixed with the polymer/biologically active agent matrix from which the solvent has been removed either prior to or following fragmentation and/or compression of the matrix. For example, an excipient can be blended with the compressed and fragmented injectable microparticle composition.

Suitable excipients include, for example, carbohydrates, amino acids, fatty acids, surfactants, and bulking agents. Such excipients are known to those of ordinary skill in the art. An acidic or a basic excipient is also suitable. The amount of excipient used is based on its ratio to the biologically active agent, on a weight basis. For amino acids, fatty acids and carbohydrates, such as sucrose, trehalose, lactose, mannitol, dextran and heparin, the ratio of carbohydrate to biologically active agent, is typically between about 1:10 and about 20:1. For surfactants, the ratio of surfactant to biologically active agent is typically between about 1:1000 and about 2:1. Bulking agents typically comprise inert materials. Suitable bulking agents are known to those of ordinary skill in the art.

The excipient can comprise a metal cation component which is separately dispersed within the polymer matrix. This metal cation component acts to modulate the release of the biologically active agent and is not complexed with the biologically active agent. The metal cation component can optionally contain the same species of metal cation, as is contained in the metal cation stabilized biologically active agent, if present, and/or can contain one or more different species of metal cation. The metal cation component acts to modulate the release of the biologically active agent from the polymer matrix of the sustained release composition and can enhance the stability of the biologically active agent in the composition. A metal cation component used in modulating release typically comprises at least one type of multivalent metal cation. Examples of metal cation components suitable to modulate release include or contain, for example, $Mg(OH)_2$, $MgCO_3$ (such as $4MgCO_3 \cdot Mg(OH)_2 \cdot 5H_2O$), $MgSO_4$, $Zn(OAc)_2$, $Mg(OAc)_2$, $ZnCO_3$ (such as $3Zn(OH)_2 \cdot 2ZnCO_3)ZnSO_4$, $ZnCl_2$, $MgCl_2$, $CaCO_3$, $Zn_3(C_6H_5O_7)_2$ and $Mg_3(C_6H_5O_7)_2$. A suitable ratio of metal cation component to polymer is between about 1:99 to about 1:2 by weight. The optimum ratio depends upon the polymer and the metal cation component utilized and can be determined by one of ordinary skill in the art without undue experimentation. A polymer matrix containing a dispersed metal cation component to modulate the release of a biologically active agent from the polymer matrix is further described in U.S. Pat. Nos. 5,656,297 issued to Bernstein, et al., on Aug. 12, 1997, and 5,912,015 issued to Bernstein, et al., on Jun. 15, 1999, the entire contents of both of which are incorporated herein by reference.

In yet another embodiment, at least one pore forming agent, such as a water soluble salt, sugar or amino acid, is included in the sustained release composition to modify the microstructure of the particles. The proportion of pore forming agent added to the mixture, e.g., a dispersion or solution, comprising a biologically active agent, a biocompatible polymer, and a polymer solvent is between about 0.1% (w/w) to about 30% (w/w).

Compression

The polymer/drug matrix can be compressed using any suitable method. For example, the polymer/drug matrix can be compressed using confined pressure compaction, e.g., molding, tableting, and roll pressing, or by extrusion, e.g., pellet milling and screw extrusion. Preferably, the polymer/drug matrix is compressed using confined pressure compaction.

The term "confined pressure compaction," as used herein, refers to compaction of a material using a confined pressure device such as, for example, a device in which internal motion and shear of the polymer/drug matrix is incidental to consolidation of the matrix in a closed mold or between two surfaces. Preferably, the confined pressure compaction is conducted without the application of heat, e.g., the application of heat other than the heat generated by the act of compressing the matrix. For example, the compression of the matrix is conducted at ambient temperature. For example, compression of the matrix is conducted at about room temperature such as about 15° C. to about 30° C., about 17° C. to about 28° C., about 20° C. to about 25° C., or about 21° C. to about 22° C. In another embodiment, the matrix is compressed at or below room temperature.

Suitable equipment for compressing the polymer/drug matrix includes, but is not limited to, die and press systems, roll presses, and tableting presses. For example, hydraulic presses such as those produced by Carver, Inc. (Wabash, Ind.) can be used in conjunction with a die. In one embodiment, a Carver Model C Press is used. The die is of any shape or size that permits the formation of a compressed polymer/drug matrix having the desired physical characteristics (e.g., density and morphology). In one embodiment, a Carver Model C Press is used in conjunction with ¼ inch to ½ inch diameter cylindrical dies to compress the polymer/drug matrix.

Fragmentation

The polymer/drug matrix can be fragmented following compression or both prior to and following compression using any suitable method. Suitable fragmentation methods include, but are not limited to, grinding, shearing, shocking, shattering, granulating, pulverizing, shredding, crushing, and/or milling. Suitable equipment for fragmenting the polymer/drug matrix includes, but is not limited to, crushers, impact mills (e.g., hammer mills, impact breakers), roll crushers, roller mills, pin mills, tumbling mills, centrifugal mills, and fluid-energy mills (e.g., jet mills), among others that are well known to one of ordinary skill in the art. An example of a suitable mill for fragmenting the polymer/drug matrix is the 24-tooth Ultra Centrifugal Mill made by Retsch, Inc. (Newtown, Pa.). Another example is the Fluid Air Granumill Jr. (Fluid Air, Inc., Aurora, Ill.).

In one embodiment, multiple stage fragmentation is used to fragment the polymer/drug matrix, for example, two or more pieces of fragmentation equipment are used to produce particles having desired physical characteristics. A particle size classifier (e.g., an appropriately sized sieve) can be used in conjunction with the fragmentation apparatus to separate particles by size.

Fragmentation of the polymer/drug matrix can be performed under various conditions of temperature, for example, cooling or cryogenic cooling can be employed to reduce the temperature of the polymer/drug matrix during processing.

In a preferred embodiment, the temperature of the polymer/drug matrix is kept at or below the transition temperature of the polymer/drug matrix, e.g., below the phase transition temperature or below the glass transition temperature of the polymer/drug matrix. In another preferred embodiment, the temperature of the polymer/drug matrix is kept below any temperature at which the agent would be subject to substantial degradation of its therapeutic, prophylactic or diagnostic effect.

In a specific embodiment, the polymer/drug matrix is also fragmented prior to the step of compressing the matrix (referred to herein as "precompression fragmenting"). Precompression fragmenting of the polymer/drug matrix can facilitate transfer of the polymer/drug matrix to a compression apparatus. For example, a film, block, or particles comprising the polymer/drug matrix is fragmented to form a flowable powder to facilitate transfer of the material to a suitable compression apparatus.

The compression and fragmenting steps can be conducted multiple times. In one embodiment, the compressed matrix is fragmented and then again compressed. The recompressed matrix is further fragmented and compressed as necessary to achieve a compressed polymer/drug matrix having a desired density and/or morphology. The resulting compressed polymer/drug matrix is then fragmented to produce the injectable microparticle composition product.

The size range of the injectable microparticles prepared by the present method can be controlled in the fragmentation step. For example, the final particle size distribution is typically a function of the total grinding or milling time, with shorter times producing, on average, larger particles and with longer grinding or milling times producing, on average, smaller particles. The size range of a sample of microparticles produced in this way can be further restricted by sorting, for example, sieving, thus achieving particles within a specified size range.

The injectable microparticles prepared according to the method described herein can be further modified to achieve a desired sustained release profile of the biologically active agent. In one embodiment, a substantial portion of the exterior surface of the injectable microparticles can be annealed or coated. Annealing is accomplished, for example, by the application of heat or an annealing solvent, wherein the annealing solvent is a solvent for the polymer of the injectable microparticle. The application of heat or an annealing solvent can be performed, for example, by using a fluidized bed system such as the Wurster process. Coating can be conducted using a suitable coating apparatus using a polymer or combination of polymers which can be the same or different from the polymer of the unmodified matrix.

"Annealing," as that term is used herein, refers to treating a substantial portion of the exterior surface of the injectable microparticles by the application of an external stress which increases the fluidity of the surface of the microparticles and upon rehardening results in a smoother and less porous outer layer.

Thus, in one embodiment, the sustained release composition of the invention comprises injectable microparticles comprising a biocompatible polymer and a biologically active agent and characterized by a porous center and a less porous outer layer, wherein the outer layer and the center consist of essentially the same materials, e.g., other components can be present either in the center or outer layer provided that the component does not function as a coating material. The variance in porosity can be achieved by annealing at least a substantial portion of the exterior surface of a solid polymer/active agent matrix. A process for annealing the surface of a sustained release composition comprising a polymer and an active agent is disclosed in U.S. Pat. No. 6,479,065 issued to Jaworowicz, et al., on Nov. 12, 2002, incorporated herein by reference in its entirety.

The present invention also includes microparticles produced according to the methods described herein. In addition, the invention is directed to pharmaceutical compositions comprising the microparticles. Pharmaceutical compositions comprising microparticles are suitable for administration to a patient. The pharmaceutical compositions described herein may also comprise pharmaceutically acceptable excipients such as, for example, diluents, stabilizers, and delivery vehicles. Pharmaceutically acceptable excipients can be selected by one of ordinary skill in the art without undue experimentation. Compositions for the delivery of microparticles are described, for example, in U.S. Pat. No. 6,495,164 issued to Ramstack, et al., on Dec. 17, 2002.

The composition of this invention can be administered in vivo, for example, to a human or to an animal, orally, or parenterally such as by injection, implantation (e.g., subcutaneously, intramuscularly, intraperitoneally, intracranially, and intradermally), administration to mucosal membranes (e.g., intranasally, intravaginally, intrapulmonary, buccally or by means of a suppository), or in situ delivery (e.g., by enema or aerosol spray) to provide the desired dosage of biologically active agent based on the known parameters for treatment with the particular agent of the various medical conditions.

The sustained release composition can be administered using any dosing schedule which achieves the desired therapeutic levels for the desired period of time. For example, the sustained release composition can be administered and the patient monitored until levels of the drug being delivered return to baseline. Following a return to baseline, the sustained release composition can be administered again. Alternatively, the subsequent administration of the sustained release composition can occur prior to achieving baseline levels in the patient.

The injectable microparticles of the present invention are used in a method for providing a therapeutically, prophylactically, or diagnostically effective amount of a biologically active agent to a subject for a sustained period. The injectable microparticle compositions described herein provide increased therapeutic benefits by reducing fluctuations in active agent concentration in blood, by providing a more desirable release profile and by potentially lowering the total amount of biologically active agent needed to provide a therapeutic benefit without the need for additional components in the composition.

As used herein, a "therapeutically effective amount," "prophylactically effective amount" or "diagnostically effective amount" is the amount of the biologically active agent or of the sustained release composition of biologically active agent needed to elicit the desired biological, prophylactic or diagnostic response following administration. For example, the desired response can be a reduction (complete or partial) of symptoms associated with affective disorders, such as, schizophrenia, depression and/or anxiety.

The present invention also includes microparticles produced according to the methods described herein. The invention is also directed to pharmaceutical compositions comprising the microparticles. Pharmaceutical compositions comprising microparticles are suitable for administration to a patient. The pharmaceutical compositions described herein may also comprise pharmaceutically acceptable excipients such as, for example, diluents, stabilizers, and delivery vehicles. Pharmaceutically acceptable excipients can be selected by one of ordinary skill in the art without undue experimentation.

EXEMPLIFICATION

The invention will now be further and specifically described by the following examples which are not intended to be limiting.

Example 1

Injectable microparticles comprising polymer and olanzapine were prepared using an efficient and facile single solvent process. PLG polymer and olanzapine were co-dissolved in a single solvent; (2) the solvent was removed by vacuum drying or sublimation to form a polymer/drug matrix; (3) the matrix was milled to produce a powder; (4) the resulting powder was compacted to form a compressed matrix; and (5) the compressed matrix was milled to form a dense, injectable microparticle formulation.

Specifically, an injectable microparticle composition comprising olanzapine (2-methyl-4-(4-methyl-1-piperazinyl)-10H-thieno[2,3-b][1,5]benzodiazepine) and poly(d,l-lactide-co-glycolide) polymer (herein referred to generically as "PLG") was prepared by co-dissolving olanzapine (Dr. Reddy's Laboratories, Ltd., Upper Saddle River, N.J.) and PLG in methylene chloride. The olanzapine loading was about 30% (w/w) of the final weight of the microparticle composition. However, it is understood that other solvents, for example, acetone, dimethylsulfoxide (DMSO), acetonitrile, and ethyl acetate are suitable for use. Table I shows specific polymer/olanzapine mixtures that were produced and which were processed into microparticles as described below.

TABLE I

Olanzapine/polymer/solvent mixtures

| Formulation | Target Olanzapine Load | PLG Polymer Type [Lactide:Glycolide Ratio; Intrinsic Viscosity; End Group] | Solvent |
|---|---|---|---|
| A | 30% (w/w) | 50:50, 0.75 dL/g; Acid end group | $CH_2Cl_2$ |
| B | 30% (w/w) | 75:25; 0.60 dL/g; Lauryl ester end group | $CH_2Cl_2$ |
| C | 30% (w/w) | 50:50; 0.61 dL/g; Lauryl ester end group | $CH_2Cl_2$ |

The olanzapine/polymer/solvent mixtures were poured into either a polytetrafluoroethylene flat mold (approximately 1 inch×1 inch×½ inch deep) or a 3 inch diameter jar to form a film. The films were then dried either in an FTS Dura-Dry Lyophilizer (Kinetic Systems, Inc., Santa Clara, Calif.) or in a vacuum oven. Films were dried under various conditions including variation of vacuum, pressure, temperature, and drying time.

The films were milled using a 24-tooth Retsch Ultra Centrifugal Mill (Retsch, Inc., Newtown, Pa.) operating at 14,000 rpm. The collection pan was filled with liquid nitrogen prior to milling. The resulting powder, collected from the collection pan, was a flowable product that aided subsequent compaction steps.

A portion of the powders produced by milling the films were retained for analysis at this point. These powders were retained for comparison with the powders made by the subsequent compacting and re-milling of the film powders described below.

A portion of the milled powders was compacted using a Carver Model C Press (Carver, Inc., Wabash, Ind.) and either about ¼ inch or about ½ inch cylindrical dies. About 50 to about 300 milligrams of milled powder was filled into the dies and compacted at a machine setting of about 5000 pounds for about 30 seconds at room temperature to form pellets.

The compacted matrix was subsequently milled using a 24-tooth Retsch Ultra Centrifugal Mill (Retsch, Inc., Newtown, Pa.) operating at 14,000 rpm. The collection pan was filled with liquid nitrogen prior to milling. The final powder was collected from the collection pan and placed into vials for analysis.

The activity of olanzapine can be assessed based on interaction with three significant neurotransmitter receptor subtypes: the $D_2$ class of dopamine receptors; the $5HT_{2A}$ subtype of serotonin receptors; and the $M_1$ subtype of muscarinic receptors. Olanzapine activity was assessed both before and after incorporation into the matrix using suitable radioligand assays.

Specifically, competition radioligand binding assays for the $D_2$, $5HT_{2A}$ and $M_1$ receptors were performed using [$^3$H]raclopride, [$^3$H]ketanserin and [$^3$H]pirenzepine, respectively. Stock solutions of native olanzapine (10 mM) and olanzapine extracted from Formulation A (Table I) microparticles (10 mM, based on % olanzapine load) were made in ethanol. Subsequent dilutions were made into 50 mM Tris HCl, pH 7.4. Binding assays varied according to the receptor/radioligand combination investigated. All assays were done with the total and non-specific binding determined in triplicate with three different receptor preparations on three separate occasions. Table II shows $K_i$ values (the concentration of competing ligand in a comparison assay which would occupy 50% of the receptors if no radioligand were present) for radioligand displacement by native olanzapine and olanzapine contained within microparticles formed from Formulation A as shown in Table I.

TABLE II $K_i$ values for radioligand displacement by native olanzapine and olanzapine contained within microparticles

| Radioligand (Receptor) | $K_i$ Native Olanzapine | $K_i$ Olanzapine in Formulation A Microparticles |
|---|---|---|
| [$^3$H]raclopride ($D_2$) | 13.6 ± 0.68 nM | 11.5 ± 4.3 nM |
| [$^3$H]ketanserin ($M_1$) | 12.8 ± 2.9 nM | 14.9 ± 1.2 nM |
| [$^3$H]pirenzepine ($5HT_{2A}$) | 1.32 ± 0.21 nM | 1.55 ± 0.32 nM |

There was no significant difference between the inhibition constants of native olanzapine and olanzapine extracted from the Formulation A microparticles in terms of their potencies in displacing radioligands from $D_2$, $M_1$ and $5HT_{2A}$ receptors.

Example 2

In vivo studies were preformed to evaluate the pharmacokinetic profile of olanzapine in rats following administration of a single subcutaneous dose of formulated olanzapine as prepared in Example 1.

Male Sprague-Dawley rats (450±50 grams) were obtained from Charles River Laboratories, Inc. (Wilmington, Mass.). Animals were divided into four test groups. Groups 1-3 received the injectable microparticles prepared according to Example 1 and detailed in Table 1 as resulting Formulations A, B and C. Group 1 was injected subcutaneously once with nominal 83 milligrams of particles produced from Formulation A. Group 2 was injected subcutaneously once with nominal 83 milligrams of particles produced from Formulation B. Group 3 was injected subcutaneously once with nominal 83 milligrams of particles produced from Formulation C. Group 4 was injected subcutaneously once with 5 milligrams of bulk olanzapine.

Specifically, animals were injected subcutaneously into the interscapular region. The injection vehicle was 3% carboxymethylcellulose ('CMC') (low viscosity) and 0.1% TWEEN® 20 (i.e., polyoxyethylene 20 sorbitan monooleate, TWEEN® is a trademark of ICI Americas, Inc.) in 0.9% aqueous sodium chloride. Each animal of Groups 1-3 received a dose comprising approximately 83 milligrams of microparticles containing about 25 milligrams of olanzapine (30% drug load) in a vehicle volume of 0.75 milliliters.

Blood samples were collected via a lateral tail vein after anesthesia with halothane. Blood samples were collected at 2, 4, 8, and 24 hours and then at 2, 4, 7, 10, 14, 17, 21, 24, and 28 days after injection. The blood was transferred to tubes containing $K_2$ EDTA and mixing beads and processed to separate the plasma. Olanzapine was detected in rat plasma using a procedure involving the analysis of an acetonitrile precipitated extract of rat plasma by high performance liquid chromatography coupled with PE/Sciex API 2000 mass spectrometer using positive ion electron spray ionization and multiple reaction monitoring mode.

Two weeks of measurable olanzapine levels were detected in vivo. FIG. 1 shows olanzapine plasma concentration versus time for a normalized dose of 50 milligrams/kilogram for microparticles produced using Formulations A, B and C. This study demonstrates that microparticles comprising olanzapine and polymer produced as described above are capable of a release of olanzapine of at least about 2 weeks in vivo.

Figure 2:
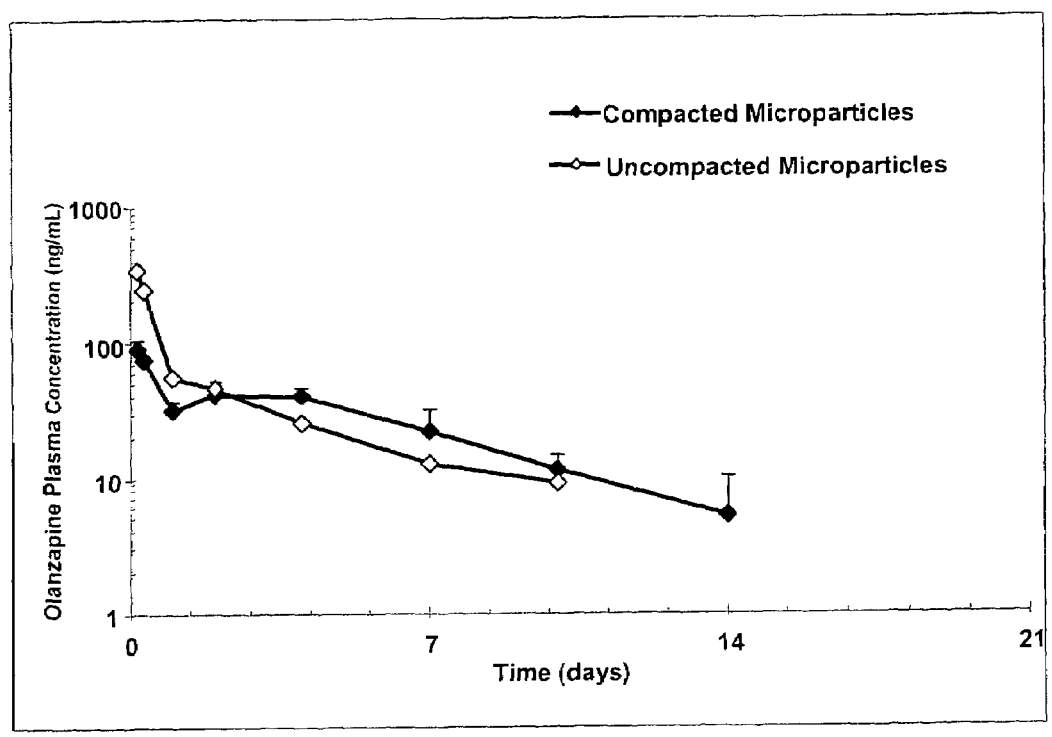
FIG. 2 is a plot of olanzapine concentration in blood plasma (nanograms/milliliter) versus time (days) for an in vivo study of two forms of a polymer/drug microparticle composition (50 milligrams olanzapine/kilogram normalized dose) administered subcutaneously to Sprague-Dawley rats. "Uncompacted" particles were produced by milling a cast film of a solution of polymer and drug. "Compacted" particles were further compacted and refragmented to produce injectable microparticles.

An additional in vivo study was conducted to investigate the effects of compaction and refragmentation of injectable microparticles. The study was conducted substantially as described above. FIG. 2 shows olanzapine plasma concentration versus time for a normalized dose of 50 milligrams/kilogram for two forms of particles produced using Formulation B. The figure compares the olanzapine plasma release from particles produced by milling the cast film as in Example 1 (shown in FIG. 2 as "uncompacted") with the release resulting from particles that were further compacted and refragmented as in Example 1 (shown in FIG. 2 as "compacted"). The data points shown in FIG. 2 represent all of the timepoints at which measurable levels of olanzapine could be detected in the blood plasma. FIG. 2 shows that a higher burst and a longer duration of release resulted from administration of the compacted and refragmented material versus that resulting from administration of the uncompacted material.

Example 3

The molecular weight of the polymer in the microparticles prepared in Example 1 was determined by gel permeation chromatography (GPC). The analysis was completed using a Waters Alliance 2695 high performance liquid chromatograph using a differential refractometer.

Samples of olanzapine-containing injectable microparticles were collected and kept refrigerated at 2-8° C. for one week prior to analysis. The residual solvent levels in the microparticle samples was about 3% by weight. The samples were assayed by GPC and found to have a significantly lower molecular weight (MW) than the starting bulk polymer. For example, the polymer of Formulation B showed a 46% decrease in average molecular weight and the polymer of Formulation C showed a 28% decrease in average molecular weight.

In view of the loss of polymer molecular weight for the microparticles produced according to Example 1, further experiments were conducted to test the effect of solvent choice on polymer degradation. It was found that among the solvents tested (methylene chloride, ethyl acetate, acetone and DMSO), a loss of polymer molecular weight was found only when methylene chloride was used as a solvent.

Figure 3:
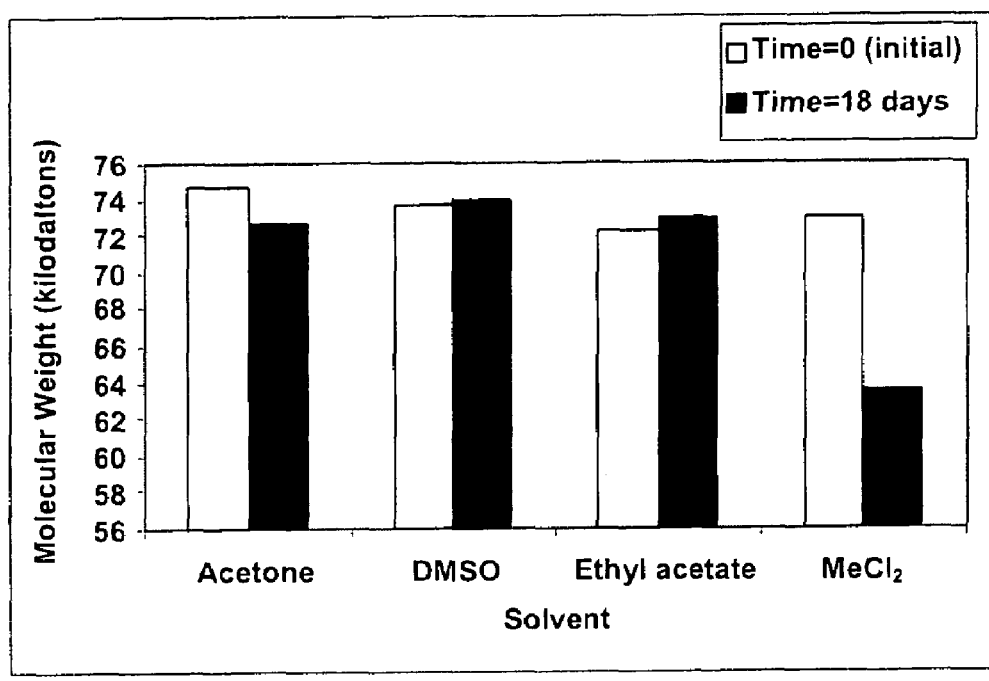
FIG. 3 is a bar chart showing the results of an 18 hour in vitro study demonstrating the effect of various solvents on the molecular weight of poly(d,l-lactide-co-glycolide) in the presence of olanzapine.

The effect was tested by preparing a solution containing 10% by weight polymer and 3% by weight olanzapine in a variety of solvents, taking a sample for gel permeation chromatography (GPC) assay immediately, and then taking another sample after 18 hours at room temperature. FIG. 3 shows a graph of the resulting polymer molecular weight (MW), in kilodaltons (kD), for each sample. The results demonstrate that the polymer degradation is most significant when methylene chloride is the processing solvent. Without wishing to be held to any particular theory, it is believed that the mechanism of action is a solvent-mediated nucleophilic attack of the ester linkages in the polymer by the tertiary amine group of the olanzapine. By using other solvents such as DMSO or ethyl acetate, the drug-catalyzed polymer degradation can be reduced. Such effects are described in U.S. Pat. No. 6,379,704, issued on Apr. 30, 2002, entitled, "Method For Preparing Microparticles Having a Selected Polymer Molecular Weight" to Wright, et al.

Microparticles comprising the polymer and olanzapine loading shown in Table 1 but using dimethylsulfoxide (DMSO) in place of methylene chloride were formed as described in Example 1. These microparticles were tested in vivo as described in Example 2.

Example 4

This example describes the production of microparticles comprising insulin and poly(lactide-co-glycolide) polymers and subsequent in vitro studies of insulin release from the microparticles.

Insulin powders were formulated using bulk insulin powder (99.4% insulin, 0.4% zinc and 0.2% impurities) (Diosynth, Inc., Des Plaines, Ill.). The bulk insulin powder was mixed in a buffer system (e.g., phosphate buffer, carbonate buffer, 1% acetic acid, or 0.1% hydrochloric acid) and zinc acetate was added to give a desired zinc to insulin molar ratio (e.g., 2:1, 10:1 or 30:1 zinc:insulin). The resulting mixture was then spray freeze dried to give an insulin powder.

For example, two insulin powders were produced. Insulin Powder Formulation I was prepared by mixing bulk insulin powder in 1% acetic acid at 10 milligrams insulin/milliliter and spray freeze drying the mixture. Insulin Powder Formulation II was prepared by mixing bulk insulin powder in 10 mM sodium bicarbonate ($NaHCO_3$) at 20 milligrams insulin/milliliter and spray freeze drying the resulting mixture. Both mixtures were spray freeze dried by combining the mixture with a nitrogen gas stream produced from a liquid nitrogen stream at 15 psi and atomizing the resulting stream at 115 psi into a tank of liquid nitrogen using a Spray Systems, Inc. Model #205070 Spray Nozzle (Wheaton, Ill.).

A mixture of about 5-30% (w/w) insulin powder was made using about 10 to 30% (w/w) polymer dissolved in methylene chloride. Polymers that were used included poly(d,l-lactide-co-glycolide) polymers having 50 mol % d,l-lactide, 50 mol % glycolide, and an acid end group (MEDISORB® 5050 DL PLG 2A polymer, MEDISORB® 5050 DL PLG 2.5A polymer, and MEDISORB® 5050 DL PLG 3.5A polymer, available from Alkermes, Inc., Cincinnati, Ohio) and PLG-co-EMPO (a functionalized PLG characterized by 8% l-lactide, 19% glycolide and 13% ethyl-2-methyl-4-pentenoate oxide (EMPO)). Some mixtures also included PLURONIC® F68 (a trademark of BASF Corp., Mount Olive, N.J.), a difunctional ethylene oxide/propylene oxide block copolymer surfactant terminating in primary hydroxyl groups. Table III shows four formulations of mixtures from which microparticles were prepared.

TABLE III

Insulin Mixture Formulations

| Formulation | Insulin Powder Formulation | Target Insulin Load | PLG Polymer | Surfactant | Measured Insulin Load |
|---|---|---|---|---|---|
| D | Formulation I | 10% (w/w) | MEDISORB ® 5050 DL PLG 2A | none | 11.3% |
| E | Formulation I | 10% (w/w) | MEDISORB ® 5050 DL PLG 2.5A | none | 11.5% |
| F | Formulation I | 10% (w/w) | PLG-co-EMPO (MW = 17kD) | none | 11.9% |
| G | Formulation II | 5% (w/w) | MEDISORB ® 5050 DL PLG 2.5A | PLURONIC ® F68 | 5.3% |

The mixtures were sonicated and films were cast in polytetrafluoroethylene molds. The cast films were dried either at room temperature or at elevated temperatures under vacuum. Post-drying, the films were milled using a 24-tooth Retsch Ultra Centrifugal Mill (Retsch, Inc., Newtown, Pa.). The dried, milled particles were then compacted at machine settings of about 3000 to about 5000 pounds using a Carver Model C Press (Carver, Inc., Wabash, Ind.) and a cylindrical ⅜ inch die for about 30 seconds to 1 minute. The compacted pellets were then milled to yield a final powdered product. The product microparticles had a size of about 200 microns.

In general, in vitro release was highly varied for the compacted and milled material and depended on the particle formulation, the protein powder formulation, and the release medium. The in vitro insulin release at 24 hours from the various microparticle formulations ranged from about 13% to about 100% of the insulin released.

Figure 4:
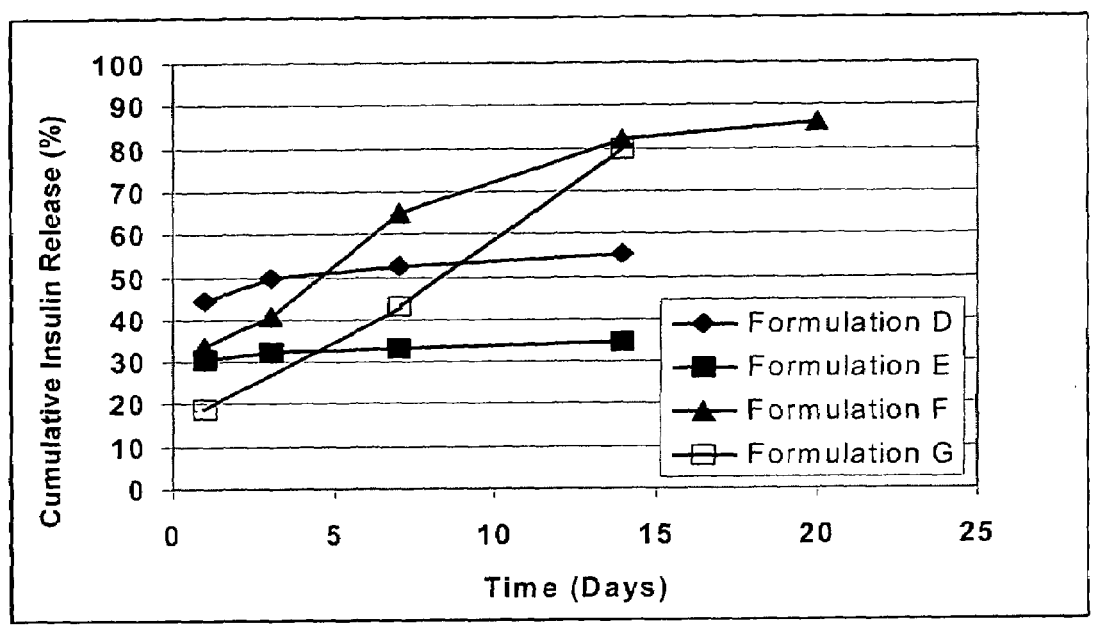
FIG. 4 is a plot showing the results of two in vitro studies measuring the cumulative release of insulin (as a percentage of total insulin) from three microparticle formulations in 0.1 M sodium phosphate, pH 7 at 37° C. and one microparticle formulation in Hepes buffer, pH 7 at 37° C. versus time (in days).

Specifically, the particle formulations of Table III were prepared and tested for in vitro release, and the results are discussed below. 10 milligrams of microparticles were added to 1 milliliter of either 0.1 M sodium phosphate, pH 7 at 37° C. or Hepes buffer, pH 7 at 37° C. UV detection at 280 nanometers was used to measure the cumulative insulin release over time. FIG. 4 shows in vitro release of insulin from microparticles produced from Formulations D, E, and F in 0.1 M sodium phosphate, pH 7 at 37° C. versus time (in days) and also from microparticles produced from Formulation G in Hepes buffer, pH 7 at 37° C. versus time (in days). Table IV shows insulin integrity for particle Formulations D, E, and F as measured by size exclusion HPLC and peak area both initially and following 14 days in 0.1 M sodium phosphate, pH 7 at 37° C. Table IV indicates good insulin integrity even after 14 days in sodium phosphate solution.

TABLE IV

Insulin Integrity of Microparticles in 0.1M sodium phosphate, pH 7 at 37° C.

| Particle Formulation | Insulin Integrity Initial Extraction (t = 0) | Insulin Integrity Extraction after 14 days in vitro |
|---|---|---|
| D | 97.9% | 80.2% |
| E | 96.7% | 85.6% |
| F | 100.0% | 91.2% |

Example 5

The following example describes the production of particles comprising the opiate antagonist naltrexone and poly (d,l-lactide-co-glycolide) polymer. The process involved the casting of a homogeneous film of naltrexone and polymer, drying the film, compacting the film, and then milling the compacted film to form an injectable composition. The powder particles were subsequently coated with a drug-free polymer shell to further control the release of naltrexone from the particles in vivo upon injection.

A drug/polymer solution was formed by co-dissolving naltrexone base (Mallinckrodt, Inc., St. Louis, Mo.) and poly(d, l-lactide-co-glycolide) polymer (MEDISORB® DL PLG polymer, Alkermes, Inc., Cincinnati, Ohio) in either acetone or methylene chloride. The concentration of polymer in solvent was about 10 to 30% (w/w). The solution was transferred to a polytetrafluoroethylene mold and was dried overnight at room temperature. The semi-dry films were then frozen in liquid nitrogen and milled using a Fluid Air Granumill Jr. (Fluid Air, Inc., Aurora, Ill.) to increase surface area for further solvent removal. The milled semi-dry films were then dried under vacuum to remove remaining solvent. The resulting dry powder was collected and compacted using a Carver Lab Model C Press (Carver, Inc., Wabash, Ind.) and a ⅜ inch cylindrical die set. The dry powder was compacted at a machine setting of about 2000-3000 pounds for 30 seconds, thus forming densified pellets. The pellets were frozen in liquid nitrogen and milled to form a free flowing, injectable, drug-loaded powder. The size of the resulting particles was less than about 200 microns. The powder was transferred to a vessel for storage. Powders were produced having 30%, 40% and 50% naltrexone by weight and using various poly(d,l-lactide-co-glycolide) polymers.

Naltrexone-containing particles produced using the above process demonstrate that dense polymer/drug particles can be produced by a process wherein the process of forming a polymer/drug matrix is decoupled from the final product morphology.

Example 6

This example describes a study of the in vitro release of naltrexone from polymer coated injectable particles produced as in Example 5 and having compositions as indicated in Tables V and VI. Polymers used included a poly(d,l-lactide-co-glycolide) polymer having 50 mol % d,l-lactide, 50 mol % glycolide, and an acid end group (MEDISORB® 5050 DL PLG 3.5A polymer and MEDISORB® 5050 DL PLG 4A polymer, Alkermes, Inc., Cincinnati, Ohio); a poly(d,l-lactide-co-glycolide) polymer having 50 mol % dl-lactide, 50 mol % glycolide, and a methyl ester end group (MEDISORB® 5050 DL PLG 4M polymer, Alkermes, Inc., Cincinnati, Ohio); PLG-co-EMPO; and MEDISORB® 6535 High IV DL PLG polymer (Alkermes, Inc., Cincinnati, Ohio).

Naltrexone load of the prepared particles was determined using either nitrogen analysis or by ultraviolet (UV) analysis of a sodium hydroxide/microparticle solution. Naltrexone load is also shown in Tables V and VI.

Naltrexone load in the microparticles was also determined by nitrogen analysis using a CHN elemental analyzer. Approximately 1 to 5 milligram samples of microparticles were combusted at 980° C. in an oxygen atmosphere to produce nitrogen and nitrogen oxides. The gas stream was reduced over copper metal at 700° C. to produce elemental nitrogen that was quantified by a thermal conductivity detector. NIST traceable acetanilide was used as the assay standard.

Naltrexone load in the microparticles was determined by dissolving approximately 10 milligrams of naltrexone loaded microparticles in 10 milliliters of 1 N sodium hydroxide for 2-4 hours. After the sample was fully dissolved, the naltrexone content was determined by UV analysis at 292 nanometers.

Twenty four hour in vitro release of naltrexone from the microparticles was determined by hydrating approximately 5 milligrams of naltrexone loaded microparticles in 3 milliliters of 150 mM sodium phosphate buffer at pH 7.0. The hydrated samples were mixed by hand shaking to fully wet the microparticles and then were placed into a 37° C. incubator for twenty four hours. At the end of the incubation period, the supernatant was removed from the system and the naltrexone content was determined by UV analysis or Reverse Phase High Performance Liquid Chromatography (RP-HPLC) using a Hewlett Packard 1090 HPLC system equipped with a 100×4.6 mm YMC phenyl column (YMC Cat# PH12S03-1046WT; YMC, Inc., Milford, Mass.).

TABLE V

Naltrexone in vitro release from microparticles made using methylene chloride

| Naltrexone Target Load | Polymer | Naltrexone Load (NaOH method) | 24 hour in vitro Release (average, n = 2) |
|---|---|---|---|
| 30% (w/w) | PLG-co-EMPO | 30% | 90% |
| 50% (w/w) | MEDISORB ® 5050 DL PLG 3.5A | 43% | 87% |
| 40% (w/w) | MEDISORB ® 5050 DL PLG 3.5A | 38% | 66% |
| 30% (w/w) | MEDISORB ® 5050 DL PLG 3.5A | 34% | 57% |
| 50% (w/w) | MEDISORB ® 5050 DL PLG 4A | 42% | 102% |
| 40% (w/w) | MEDISORB ® 5050 DL PLG 4A | 29% | 89% |
| 30% (w/w) | MEDISORB ® 5050 DL PLG 4A | 27% | 79% |
| 30% (w/w) | MEDISORB ® 5050 DL PLG 4M | 29% | 84% |

TABLE VI

Naltrexone in vitro release from microparticles made using acetone

| Naltrexone Target Load | Polymer | Naltrexone Load (NaOH method) | 24 hour in vitro Release (average, n = 2) |
|---|---|---|---|
| 50% (w/w) | MEDISORB ® 5050 DL PLG 3.5A | 51% | 78% |
| 40% (w/w) | MEDISORB ® 5050 DL PLG 3.5A | 39% | 103% |
| 30% (w/w) | MEDISORB ® 5050 DL PLG 3.5A | 24% | 81% |
| 50% (w/w) | MEDISORB ® 5050 DL PLG 4A | 45% | 108% |
| 40% (w/w) | MEDISORB ® 5050 DL PLG 4A | 42% | 93% |
| 30% (w/w) | MEDISORB ® 5050 DL PLG 4A | 31% | 97% |
| 30% (w/w) | MEDISORB ® 6535 High IV DL PLG | 29% | 73% |

Polymer coated particles, shown in Table VII, were prepared as described in Example 5 using a poly(d,l-lactide-co-glycolide) polymer having 50 mol % d,l-lactide, 50 mol % glycolide, and an acid end group (MEDISORB® 5050 DL PLG 3.5A polymer, Alkermes, Inc., Cincinnati, Ohio), naltrexone, and methylene chloride as the solvent. The resulting powder contained a target drug load of up to 50% by weight. The milled powder particles were polymer coated using a Fluid Air Model 002 Dry/Granulator/Coater equipped with a 0.5 L bowl (Fluid Air, Inc., Aurora, Ill.). The particles were fluidized in a bed of nitrogen gas and a coating solution of polymer in acetone was applied using an air/air atomizer.

The batch was split and coated with varying amounts of either a poly(d,l-lactide-co-glycolide) polymer having 50 mol % d,l-lactide, 50 mol % glycolide, and an acid end group (MEDISORB® 5050 DL PLG 2A polymer, Alkermes, Inc., Cincinnati, Ohio) or a poly(d,l-lactide-co-glycolide) polymer having 50 mol % d,l-lactide, 50 mol % glycolide, and an methyl ester end group (MEDISORB® 5050 DL PLG 2M polymer, Alkermes, Inc., Cincinnati, Ohio) as shown in Table VII.

TABLE VII

Naltrexone in vitro release from polymer coated microparticles

| Target Naltrexone Load | Coating Polymer | Naltrexone Load ($N_2$ method) | 24 hour in vitro Release (average, n = 2) |
|---|---|---|---|
| 50% (w/w) | none | 39% | 107% |
| 45% (w/w) | MEDISORB ® 5050 DL PLG 2A polymer | 31% | 79% |
| 42.5% (w/w) | MEDISORB ® 5050 DL PLG 2A polymer | 30% | 60% |
| 40% (w/w) | MEDISORB ® 5050 DL PLG 2A polymer | 30% | 53% |
| 45% (w/w) | MEDISORB ® 5050 DL PLG 2M polymer | 33% | 87% |
| 42.5% (w/w) | MEDISORB ® 5050 DL PLG 2M polymer | 32% | 74% |
| 40% (w/w) | MEDISORB ® 5050 DL PLG 2M polymer | 32% | 48% |

Example 7

This example describes a study of the in vivo release of naltrexone from polymer coated injectable particles produced as in Example 5.

To evaluate the release of drug from polymer coated particles, a 100 gram batch of powder was produced as described in Example 5 using a poly(d,l-lactide-co-glycolide) polymer having 50 mol % d,l-lactide, 50 mol % glycolide, and an acid end group (MEDISORB® 5050 DL PLG 3.5A polymer, Alkermes, Inc., Cincinnati, Ohio), naltrexone, and methylene chloride as the solvent. The resulting powder contained a target drug load of up to 50% by weight. The milled powder particles were polymer coated using a Fluid Air Model 002 Dry/Granulator/Coater equipped with a 0.5 L bowl (Fluid Air, Inc., Aurora, Ill.). The particles were fluidized in a bed of nitrogen gas and a coating solution of polymer in acetone was applied using an air/air atomizer.

The batch was split and coated with varying amounts of either a poly(d,l-lactide-co-glycolide) polymer having 50 mol % d,l-lactide, 50 mol % glycolide, and an acid end group (MEDISORB® 5050 DL PLG 2A polymer, Alkermes, Inc., Cincinnati, Ohio) or a poly(d,l-lactide-co-glycolide) polymer having 50 mol % d,l-lactide, 50 mol % glycolide, and an methyl ester end group (MEDISORB® 5050 DL PLG 2M polymer, Alkermes, Inc., Cincinnati, Ohio) as shown in Table VIII.

TABLE VIII

Coated Particle Formulations

| Particle Formulation | Target Naltrexone Load | Coating Polymer | Coating Polymer Concentration (% by weight) |
|---|---|---|---|
| H | 50 | none | none |
| I | 45 | MEDISORB ® 5050 DL PLG 2A polymer | 10 |
| J | 42.5 | MEDISORB ® 5050 DL PLG 2A polymer | 15 |
| K | 40 | MEDISORB ® 5050 DL PLG 2A polymer | 20 |
| L | 45 | MEDISORB ® 5050 DL PLG 2M polymer | 10 |
| M | 45.2 | MEDISORB ® 5050 DL PLG 2M polymer | 15 |
| N | 40 | MEDISORB ® 5050 DL PLG 2M polymer | 20 |

Particles produced according to the process described above and containing approximately 15-20 milligrams of naltrexone were suspended in an aqueous injection vehicle containing 3% carboxymethylcellulose (low viscosity), 0.1% polysorbate 20, and 0.9% sodium chloride. The suspension was injected subcutaneously into the mid-scapular region of male Sprague-Dawley rats (450±50 g body weight, immunosuppressed).

Blood samples were collected via a lateral tail vein bleed after anesthesia with halothane. The blood was transferred to serum separator tubes and allowed to clot for 30 minutes at room temperature, centrifuged at >6000 g for 5 minutes at 2-8° C., then stored at −70° C. Blood samples were collected at 2, 8, and 24 hours and then at 2, 4, 7, 10, 14, 21, 24, 28, 31, and 35 days after injection. Serum naltrexone concentration were determined by mass spectrometry.

Figure 5:
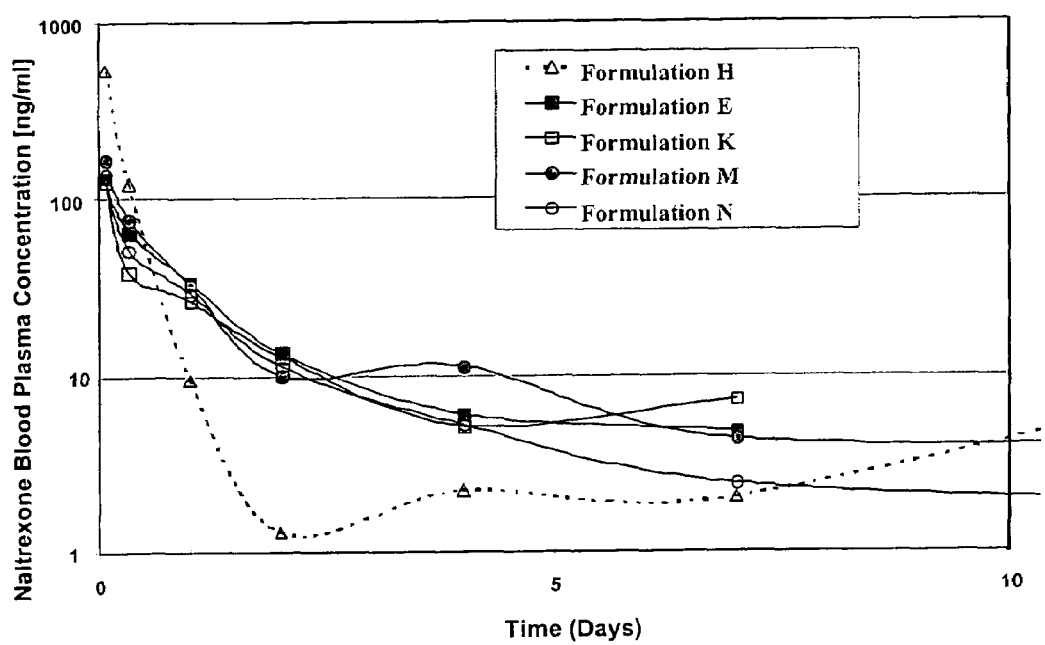
FIG. 5 is a plot of naltrexone concentration in blood plasma (nanograms/milliliter) versus time (days) for an in vivo study of four polymer/drug microparticle compositions coated with various polymers and one uncoated control microparticle composition administered subcutaneously to Sprague-Dawley rats.

FIG. 5 shows the in vivo release profile of naltrexone from variously coated particles over a 10 day study period. The in vivo results demonstrate that the release profile of naltrexone can be further controlled by applying a polymer coating to the relatively dense drug/polymer particles. The in vivo results also indicate that the initial burst of naltrexone release was reduced and also that the overall naltrexone release profile was improved.

Example 8

This example describes the production of microparticles comprising bovine serum albumin (herein "BSA," obtained from EM Science, Gibbstown, N.J.) and an in vivo study preformed to test release of BSA from the microparticles.

A zinc/BSA complex was formed at a 10/1 molar ratio using spray freeze drying as earlier described. 74.7 grams of powdered zinc/BSA complex was suspended in 2371 milliliters of methylene chloride with 474 grams of a poly(d,l-lactide-co-glycolide) polymer having 50 mol % d,l-lactide, 50 mol % glycolide, and an acid end group (MEDISORB® 5050 DL PLG 2A polymer) and 4.7 grams $ZnCO_3$. This suspension was combined with a nitrogen gas stream and sprayed at 30 psi using a Spray Systems, Inc. Model #205070 Spray Nozzle (Wheaton, Ill.) into liquid nitrogen to form particles. The particles were recovered form the liquid nitrogen and the methylene chloride was extracted from the particles using excess ethanol. The resulting polymer/drug microparticles (15% zinc/BSA complex and 1% $ZnCO_3$ target load) were dried under vacuum for five days.

A portion of the polymer/drug microparticles thus formed were then compacted using a Carver Model C Press (Carver, Inc., Wabash, Ind.) at a machine setting of 4000 pounds to form wafers having a diameter of ⅜ inch and a thickness of about ⅛ of an inch. A portion of the wafers were fragmented by freezing the wafers in liquid nitrogen and then fracturing the frozen wafers using a razor blade thus forming implantable microparticles. The implantable microparticles had a size range of from about 200 to about 500 microns.

The compositions (polymer/drug microparticles, wafers and implantable microparticles) thus formed were administered to laboratory rats. Male Sprague-Dawley rats (400±50 grams) were obtained from Charles River Laboratories, Inc. (Wilmington, Mass.). The animals were immunosuppressed using cyclosporine (SANDIMMUNE®, Novartis Pharmaceuticals Corp., East Hanover, N.J.). Animals were divided into three test groups (n=3/group).

Animals in Group A were injected subcutaneously with the polymer/drug microparticles into the interscapular region. Each animal received a dose comprising approximately 50 milligrams of particles containing 7.5 milligrams BSA in a vehicle volume of 0.75 milliliters. The injection vehicle was 3% carboxymethylcellulose ('CMC') (low viscosity) and 0.1% TWEEN® 20 (i.e., polyoxyethylene 20 sorbitan monooleate, TWEEN® is a trademark of ICI Americas, Inc.) in 0.9% aqueous sodium chloride.

The animals in Group B were implanted subcutaneously with 50 milligrams compressed wafers (total amount of BSA administered was 7.5 mg) into the interscapular region.

The animals in Group C were implanted subcutaneously with 50 milligrams implantable microparticles (total amount of BSA administered was 7.5 mg) into the interscapular region.

Blood samples were collected via a lateral tail vein after anesthesia with halothane. Blood samples were collected at predose, at 2, 4, 6, 10, and 24 hours and then at 2, 4, 7, 10, 14, 17, 21, 24, and 28 days after administration. The blood was transferred to serum separator tubes and allowed to clot for 30 minutes at room temperature, centrifuged at 6000 g for 5 minutes at room temperature, and the serum stored at less than −70° C. Serum samples were analyzed using a BSA Enzyme-Linked Immuno-Sorbent Assay (ELISA) kit (Catalog #F030) provided by Cygnus Technologies (Wrentham, Mass.).

Figure 6:
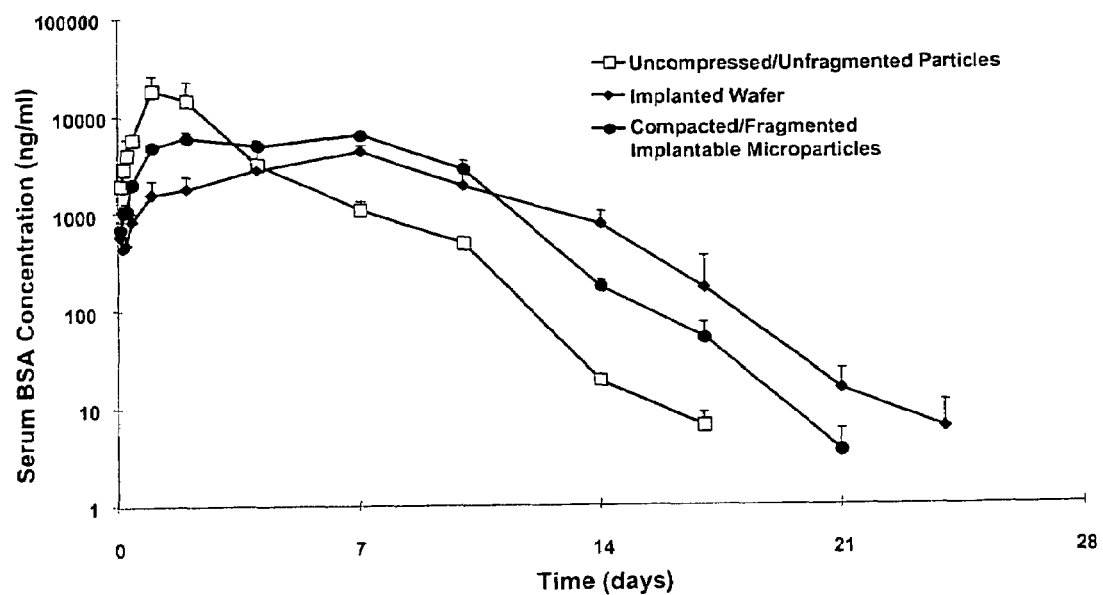
FIG. 6 is a plot of Bovine Serum Albumin (herein "BSA") concentration in blood plasma (nanograms/milliliter) versus time (days) for an in vivo study of three polymer/drug compositions (15 milligrams BSA/kilogram normalized dose) administered to rats.

FIG. 6 shows BSA concentration in blood serum, in nanograms/milliliter, versus time, in days. The data demonstrate that the implantable microparticles gave a release profile with a $C_{MAX}$ (i.e., maximum BSA concentration in blood serum) lower than that of the uncompressed, unfragmented polymer/drug particles but higher than the implanted wafer. The implantable microparticles also showed higher sustained concentrations of BSA, and a longer duration of release than that provided by the uncompressed, unfragmented polymer/drug particles.

While this invention has been particularly shown and described with references to preferred embodiments thereof, it will be understood by those skilled in the art that various changes in form and details may be made therein without departing from the scope of the invention encompassed by the appended claims.

We claim:

1. A method for preparing an injectable microparticle composition for the sustained release of a biologically active agent, comprising the steps of:
   (a) preparing a mixture of a biologically active agent, a biocompatible polymer and a solvent, thereby forming a single phase solvent system;
   (b) removing the solvent from the mixture, thereby forming a polymer/biologically active agent matrix;
   (c) compressing the matrix using confined pressure compaction at ambient temperature, thereby forming a compressed matrix; and
   (d) fragmenting the compressed matrix, thereby forming the injectable microparticle composition.

2. The method of claim 1 wherein the biologically active agent is dissolved in the mixture.

3. The method of claim 1 wherein the biologically active agent is suspended in the mixture.

4. The method of claim 1 further comprising the step of fragmenting the matrix prior to compressing the matrix.

5. The method of claim 1 wherein the biocompatible polymer is biodegradable.

6. The method of claim 1 wherein the biocompatible polymer is selected from the group consisting of poly(lactide)s, poly(glycolide)s, poly(lactide-co-glycolide)s, poly(lactic acid)s, poly(glycolic acid)s, polycarbonates, polyesteramides, polyanhydrides, poly(amino acids), polyorthoesters, polyacetals, polycyanoacrylates, polyetheresters, polycaprolactone, poly(dioxanone)s, poly(alkylene alkylate)s, polyurethanes, and blends and copolymers thereof.

7. The method of claim 6, wherein the polymer is poly(lactide-co-glycolide)-co-EMPO.

8. The method of claim 1 wherein the solvent is removed by evaporation.

9. The method of claim 1 wherein the solvent is removed by sublimation.

10. The method of claim 1 wherein the mixture is cast as a film prior to removal of the solvent.

11. The method of claim 1 wherein the matrix is compressed using a press and die apparatus.

12. The method of claim 1 wherein the compressed matrix is fragmented by milling.

13. The method of claim 12 wherein the milling is selected from the group consisting of jet milling, centrifugal milling and hammer milling.

14. The method of claim 1 wherein the compressed matrix is fragmented under cryogenic conditions.

15. The method of claim 1 wherein the compressed matrix is fragmented to produce microparticles having a volume median particle size of about 1 to about 1000 microns.

16. The method of claim 1 wherein the compressed matrix is fragmented to produce microparticles having a volume median particle size of about 500 microns or less.

17. A method for forming an injectable microparticle composition for the sustained release of a biologically active agent, comprising the steps of:
   (a) forming a mixture of a biologically active agent, a biocompatible polymer and a polymer solvent;
   (b) forming droplets of the mixture;
   (c) freezing the droplets, thereby forming frozen droplets;
   (d) extracting the polymer solvent from the frozen droplets into a non-solvent, thereby forming a polymer/biologically active agent matrix;
   (e) compressing the matrix, thereby forming a compressed matrix; and
   (f) fragmenting the compressed matrix, thereby forming the injectable microparticle composition.

18. The method of claim 17 wherein the biocompatible polymer is biodegradable.

19. The method of claim 17 wherein the biocompatible polymer is selected from the group consisting of poly(lactide)s, poly(glycolide)s, poly(lactide-co-glycolide)s, poly(lactic acid)s, poly(glycolic acid)s, polycarbonates, polyesteramides, polyanhydrides, poly(amino acids), polyorthoesters, polyacetals, polycyanoacrylates, polyetheresters, polycaprolactone, poly(dioxanone)s, poly(alkylene alkylate)s, polyurethanes, and blends and copolymers thereof.

20. The method of claim 17 wherein the droplets are frozen using a liquefied gas.

21. The method of claim 17 wherein the droplets are formed by atomizing the mixture.

22. The method of claim 17 wherein the droplets are microdroplets.

23. The method of claim 17 wherein the matrix is compressed using confined pressure compaction.

24. The method of claim 17 wherein the matrix is compressed using a press and die apparatus.

25. The method of claim 17 wherein the matrix is compressed in the presence of a coolant.

26. The method of claim 17 wherein the compressed matrix is fragmented by milling.

27. The method of claim 26 wherein the compressed matrix is fragmented by milling selected from the group consisting of jet, centrifugal and hammer milling.

28. The method of claim 17 wherein the compressed matrix is fragmented in the presence of a coolant.

29. The method of claim 17 wherein the compressed matrix is fragmented under cryogenic conditions.

30. The method of claim 17 wherein the compressed matrix is fragmented matrix is fragmented to produce microparticles having a volume median particle size of about 1 micron to about 1000 microns.

31. The method of claim 17 wherein the compressed matrix is fragmented to produce microparticles having a volume median particle size of about 500 microns or less.

32. The method of claim 17 wherein the biologically active agent is suspended in the mixture.

33. The method of claim 17 wherein the biologically active agent is dissolved in the mixture.

34. A method for treating a patient in need of therapy comprising: administering to the patient a therapeutically effective amount of the injectable microparticle composition made by the method of claim 17.

35. A method for treating a patient in need of a sustained release of a biologically active agent, comprising:
  administering to the patient a therapeutically effective amount of an injectable microparticle composition for sustained release of a biologically active agent prepared by a process including the steps of:
  (a) preparing a mixture of a biologically active agent, a biocompatible polymer and a solvent, thereby forming a single phase solvent system;
  (b) removing the solvent from the mixture, thereby forming a polymer/biologically active agent matrix;
  (c) compressing the matrix using confined pressure compaction at ambient temperature, thereby forming a compressed matrix; and
  (d) fragmenting the compressed matrix, thereby forming the injectable microparticle composition.

36. The method of claim 35 wherein the biologically active agent is dissolved in the mixture.

37. The method of claim 35 wherein the biologically active agent is suspended in the mixture.

38. The method of claim 35 wherein the process for preparing the injectable microparticle composition further comprises the step of fragmenting the polymer/biologically active agent matrix prior to compressing the matrix.

39. The method of claim 35 wherein the biologically active agent is an antipsychotic drug.

40. The method of claim 39 wherein the biologically active agent is selected from the group consisting of aripiprazole, olanzapine and risperidone.

41. The method of claim 39 wherein the patient suffers from an affective disorder.

42. The method of claim 41 wherein the patient suffers from a condition selected from the group consisting of schizophrenia, depression, and anxiety.

* * * * *

UNITED STATES PATENT AND TRADEMARK OFFICE
CERTIFICATE OF CORRECTION

PATENT NO. : 7,658,998 B2  Page 1 of 1
APPLICATION NO. : 10/762220
DATED : February 9, 2010
INVENTOR(S) : Brown et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1361 days.

Signed and Sealed this

Thirtieth Day of November, 2010

David J. Kappos
*Director of the United States Patent and Trademark Office*